United States Patent [19]

Kurtze et al.

[11] Patent Number: 4,721,106

[45] Date of Patent: Jan. 26, 1988

[54] PIEZOELECTRIC TRANSDUCER FOR DESTRUCTION OF CONCRETIONS INSIDE THE BODY

[75] Inventors: Günther Kurtze, Weinheim/Bergstrasse; Rainer Riedlinger, Karlsruhe, both of Fed. Rep. of Germany

[73] Assignee: Richard Wolf GmbH, Knittlingen, Fed. Rep. of Germany

[21] Appl. No.: 63,693

[22] Filed: Jun. 15, 1987

Related U.S. Application Data

[63] Continuation of Ser. No. 752,584, Jul. 8, 1985, abandoned.

[30] Foreign Application Priority Data

Jul. 14, 1984 [DE] Fed. Rep. of Germany ....... 3425992

[51] Int. Cl.[4] ...................... A61B 17/00; A61H 23/02

[52] U.S. Cl. ................................ 128/328; 128/24 A; 310/327; 367/176; 604/22

[58] Field of Search .................. 128/24 A, 303.1, 305, 128/328; 310/327, 334, 369, 371; 367/162, 176; 604/22, 30, 35, 36

[56] References Cited

U.S. PATENT DOCUMENTS

| | | | |
|---|---|---|---|
| 2,416,337 | 2/1947 | Mason | 367/162 |
| 2,707,755 | 5/1955 | Hardie | 310/327 |
| 2,728,869 | 12/1955 | Pohlman | 310/327 |
| 2,946,904 | 7/1960 | Renaut | 310/327 |
| 2,972,068 | 2/1961 | Howry | 367/162 |
| 2,984,756 | 5/1961 | Bradfield | 310/327 |
| 3,038,551 | 6/1962 | McCoy | 367/176 |
| 3,403,271 | 9/1968 | Lobdell | 310/8.2 |
| 3,876,890 | 4/1975 | Brown | 310/334 |
| 3,995,179 | 11/1976 | Flournoy | 310/8.2 |
| 4,382,201 | 5/1983 | Trzaskos | 310/327 |
| 4,528,652 | 7/1985 | Horner | 367/162 |

FOREIGN PATENT DOCUMENTS

| | | | |
|---|---|---|---|
| 3025233 | 1/1981 | Fed. Rep. of Germany . | |
| 3114657 | 1/1982 | Fed. Rep. of Germany . | |
| 8205955 | 7/1982 | Fed. Rep. of Germany . | |
| 3119295 | 12/1982 | Fed. Rep. of Germany . | |
| 2913251 | 8/1985 | Fed. Rep. of Germany . | |
| 1215631 | 11/1959 | France | 310/327 |
| 95795 | 6/1982 | Japan | 367/176 |
| 423033 | 9/1974 | U.S.S.R. | 310/327 |

OTHER PUBLICATIONS

Methods of Experimental Physics, vol. 19, Ultrasonics, Peter D. Edmonds (ed.), Academic Press 1981, Chapter 1, Piezoelectric Transducers, pp. 62-64.

Textbook "Werkstoffprufung mit Ultraschall" (Material Testing with Ultrasound) by Josef and Herbert Krautkramer, Third Revised Printing, Springer-Verlag Berlin, Heidelberg, New York, 197r, pp. 71, 218, and 219.

Book "Ultrasound: Its Application in Medicine and Biology", Part 1 (ed. F. J. Fry), Amsterdam 1978, pp. 289, 325, 337, 338.

Ultrasonics, Jul. 1974, pp. 161-167, article by A. F. Brown and J. P. Weight with the title "Generation and Reception of Wideband Ultrasound".

Research report Forschungsbericht T 84-055 of the Federal Ministry for Research and Technology, Apr. 1984, pp. 1-15, in particular p. 13, last paragraph.

*Primary Examiner*—Clyde I. Coughenour

*Attorney, Agent, or Firm*—Willian Brinks Olds Hofer Gilson & Lione Ltd.

[57] ABSTRACT

A piezoelectric transducer for destruction of concretions inside the body. The transducer essentially comprises a spheroidal cap having piezoelectric ceramic elements situated at its radially inner front side. To prevent overpressure pulses radiated at the front side of the transducer being followed by underpressure pulse reflected from the rear side of the cap, the cap is produced from metal, preferably from a copper alloy. The impact wave resistances of the cap metal and of the ceramic material should largely correspond. Furthermore, the rear-side surface of the rear wall of the cap is so shaped geometrically and/or provided with a coating, that the sonic waves reflected therefrom are no longer focussed.

7 Claims, 3 Drawing Figures

PIEZOELECTRIC TRANSDUCER FOR DESTRUCTION OF CONCRETIONS INSIDE THE BODY

This application is a continuation of application Ser. No. 752,584, filed July 8, 1985, now abandoned.

BACKGROUND OF THE INVENTION

1. Field of the Invention

The invention relates to a piezoelectric transducer for destruction of concretions inside the body, comprising a spheroidal cap having piezoelectric ceramic elements situated on its radially inner side, hereinafter called the front side which in use faces towards the concretion to be destroyed.

2. Description of the Prior Art

German Patent Specification No. 3319871, the disclosure of which is incorporated herein by reference, discloses a transducer of the above type which comprises a mosaic of piezoceramic elements on its front side or surface with each element having a height of about 3 to about 10 mm and a lateral extension not exceeding their height. The gaps between these elements are filled with an electrically insulating material such as silicone rubber.

The excitation of a piezoelectric transducer of this kind by means of an HT pulse may have the result that an almost rectangular overpressure or underpressure pulse is generated initially depending on the direction of polarisation, the duration of which is determined by the period of propagation of the compression or expansion wave within the ceramic material. The same also occurs at the rear side or surface (i.e. the radially outer side) of the transducer. It is reflected there under phase reversal and appears subsequently with reversed phase at the front side.

An overpressure pulse is thus always followed by an underpressure pulse, and since the major proportion of the energy is also reflected at the front side under phase reversal, this action is repeated a number of times. Instead of a single pulse, what is generated is a decaying oscillation whose fundamental frequency is established by the lowest natural thickness oscillation (thickness $\approx \frac{1}{2}$ wavelength) of the piezoceramics.

It may be expected that cavitation phenomena occur in the underpressure phases of this decaying oscillation. Provided that this actually occurs on the concretion which is to be destroyed, this may lead to an accelerated destruction, and may thus have a favourable consequence. It cannot be precluded however that the cavitation threshold may already be exceeded even in the anteriorly situated tissue. Cavitation within tissue may however lead to bleeding or to tissue destruction.

SUMMARY OF THE INVENTION

It is an object of the invention to prevent the occurrence of underpressure pulses, or at least to reduce them to such a degree that cavitations may be averted.

In accordance with the invention, in the case of a piezoelectric transducer of the type mentioned in the foregoing, the cap is of metal, preferably of a copper alloy, and the impact wave resistance of the cap material corresponds at least substantially to the impact wave resistance of the material of the ceramic elements. The rear-side surface of the cap is so shaped geometrically and/or coated that the spheroidal waves reflected thereon are not focused. Thus the metal cap is provided with means either to prevent a focussing of the reflected spheroidal waves from a back surface or to scatter its reflected waves from the back surface to prevent cavitation within the tissue of the patient.

In the transducer of the invention, a generated underpressure pulse is not followed by an underpressure pulse generated by reflection, since the ceramic elements have their rear side delimited in a reflection-free manner. The elements then no longer have any natural frequencies, and their deformations follow an electrically preset pulse form.

BRIEF DESCRIPTION OF THE DRAWINGS

In order that the invention may be more readily understood, reference will now be made to the accompanying drawings which ilustrate preferred embodiments of the invention. In the drawings.

DETAILED DESCRIPTION OF THE PREFERRED EMBODIMENTS

Figure 1:
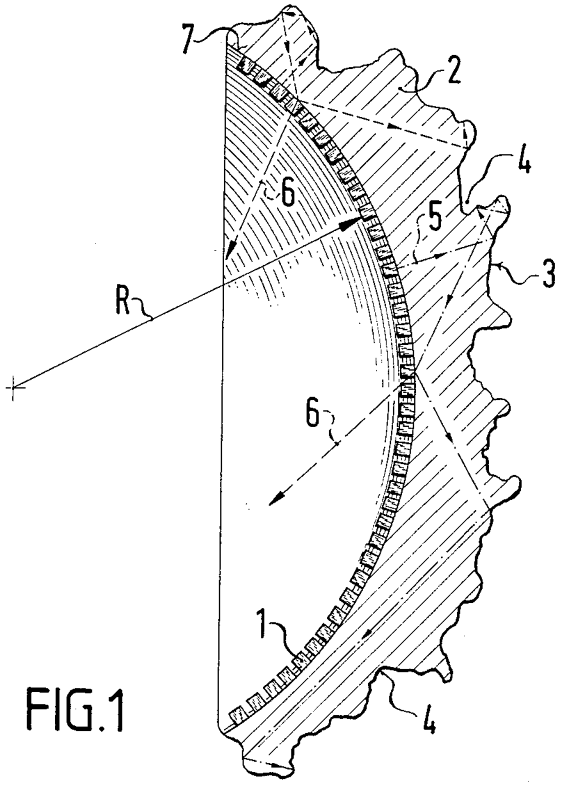
FIG. 1 is a cross-sectional view of a transducer according to a first embodiment of the invention.

Referring first to FIG. 1, a reflection-free delimitation of the piezoelectric ceramic elements 1 situated on the front face of a part-spherical cap 2 and aligned on a radius R may advantageously be secured by means of copper alloys, such as brass or bronze. If the supporting cap 2 is constructed as a brass cap, the alloy is selected in such a manner that its impact wave resistance at least substantially corresponds to that of the ceramics, and if the ceramic elements 1 are secured thereon by means of a very thin solderable or conductive adhesive layer, no reflection then occurs at the rear side of the ceramic elements. The forwardly radiated pulse is even amplified as compared to a transducer having a cap of a plastics material.

The rearwardly radiated sonic pulse penetrates into the cap 2. Since the latter may not have the desired thickness, the sonic pulse would normally be reflected on the cap rear side under phase reversal, meaning that the underpressure pulse may well be delayed, but not prevented.

There are several possibilities within the scope of the invention for suppression of this delayed pulse. The rear side of the cap may be coated with a sound-absorbent material, and provision may be made for an even transition from the cap material into the absorbent material, by means of depressions, grooves or the like, whereof the depth is greater than the pulse length. This method is comparatively costly, however. In this context, a better solution would be that the rear-side surface of the cap is so formed, for example by curvatures extending contradirectionally to the cap curvature, that the underpressure surge caused by reflection is no longer focussed.

FIG. 1 shows a solution in which the rear-side surface 3 of the cap 2 has irregular depressions or grooves 4, that is to say being greatly fissured. The sonic pulse 5, which is rearwardly radiated by the ceramic elements, is partially reflected in multiple form as shown by the arrows at the rear-side surface 3 as well as at a front-side surface 7 of the cap 2, and the sound fraction 6 issuing from the front is no longer focussed, so that the underpressure pulse previously referred to will no longer occur.

Figure 2:
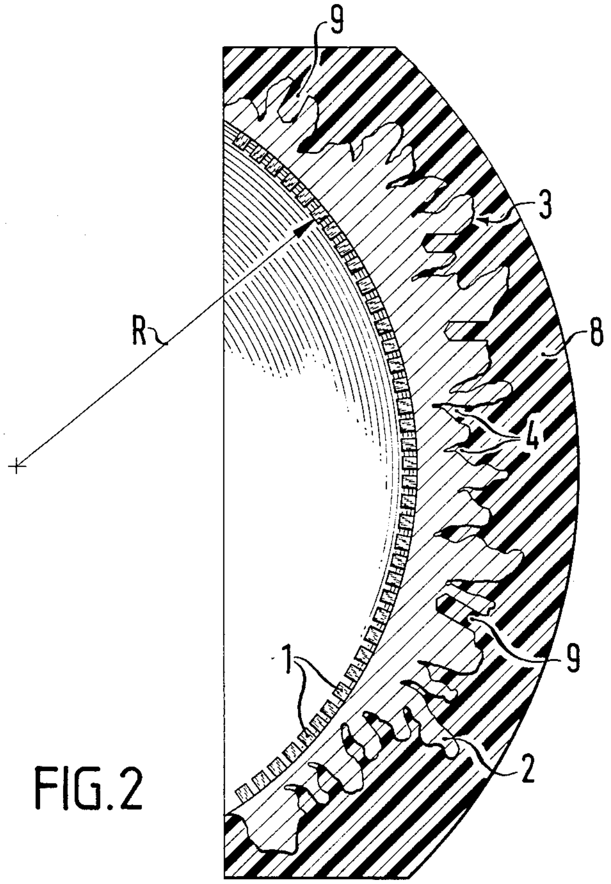
FIG. 2 is a cross-sectional view of a second embodiment.

The embodiment shown in FIG. 2 corresponds substantially to the embodiment of FIG. 1, but the rear-side cap surface 3 is complementarily provided with a sound-absorbing layer 8 of a synthetic resin or the like. If the depressions or grooves 4 are deeper than the sonic pulse length, the sonic waves issuing at the rear from the cap material will pass with little reflection into the layer 8 and be absorbed therein. Instead of or as well as the depressions 4, bores 9 could also be provided at the rear side of the cap 2.

Figure 3:
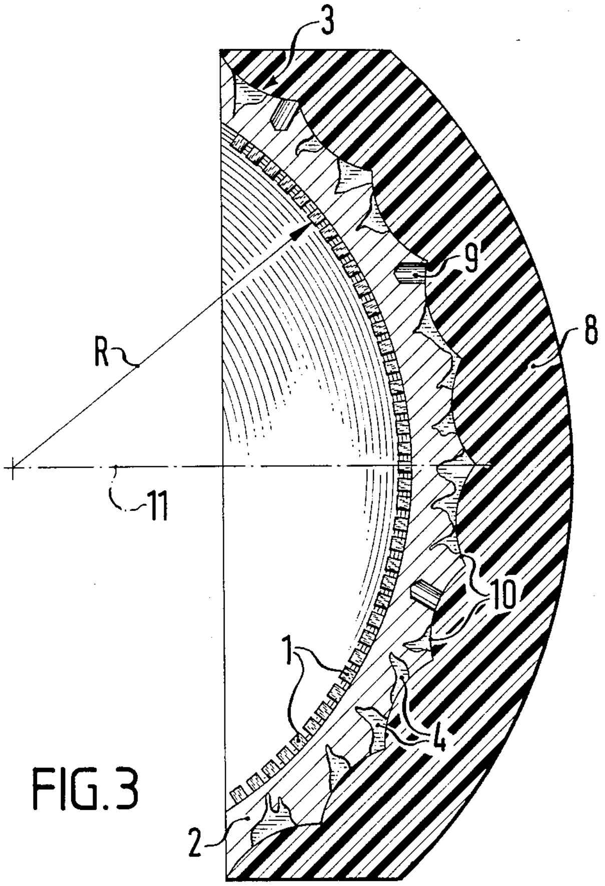
FIG. 3 is a cross-sectional view of a third embodiment.

Another advantageous solution is shown in Figure 3, in which the rear-side surface 3 of the cap 2 is divided into a number of part surfaces 10, the curvatures of which are orientated contradirectionally to the front-side curvature of the cap and whose radii of curvature differ substantially from the front-side radius of curvature of the cap, according to the illustration. It is thereby possible to prevent any symmetry of these curvatures with respect to the axis 11 of the cap. The part surfaces 10, for their part, are also provided in this case with irregular depressions, wedge-shaped grooves 4 and/or with bores 9 (blind holes) whose depth corresponds to at least the thickness of the ceramic elements 1. Furthermore, the cap is provided at its rear side with a layer of hard material 8, which is electrically insulating as well as sound absorbing. This layer may for example consist of synthetic resin with hard inorganic fillers.

As for the rest, in transducers of this kind, the cap 2 of metal will act as a so-called "hot" electrode, whereas the front-side metallisation of the cap will be placed at earth or ground potential. Furthermore, the ceramic elements arranged in a mosaic or matrix may be embedded by casting in a soft and electrically insulating material.

We claim:

1. In a piezoelectric transducer for destruction of concretions inside a body, said transducer comprising a cap having an inner surface with a partially-spherical curvature with a given radius from a point, said cap having a back surface, a plurality of piezoelectric ceramic elements for producing sonic pulses being mounted on the inner surface to form a mosaic of elements with the output of the sonic pulses from said mosaic of elements being focussed at said point, the improvements comprising the cap being of a metal with an wave impact resistance of the metal corresponding at least substantially to the wave impact resistance of the material of the ceramic elements, and the cap having means for scattering sonic pulses entering into the cap from the elements to prevent the back surface of the cap from reflecting a focussed wave of sonic pulses at said point.

2. In a piezoelectric transducer according to claim 1, wherein the cap is made from a copper alloy.

3. In a piezoelectric transducer according to claim 1, wherein the means for scattering incldues said back surface of the cap having irregular recesses therein.

4. In a piezoelectric transducer according to claim 3, wherein said back surface is coated with an insulating and sound-absorbing material and wherein said irregular recesses cause a uniform transition of the impact wave resistance into said sound-absorbing material.

5. In a piezoelectric transducer according to claim 1, wherein the means for scattering include the back surface of the cap being divided into curved partial surfaces having curvatures which are assymetric relative to an axis of the cap, said curved partial surfaces having radii of curvature which differs substantially from the radius of curvature of the inner surface of the cap.

6. In a piezoelectric transducer according to claim 5, wherein said partial surfaces have irregular recesses.

7. In a piezoelectric transducer according to claim 6, wherein the partial surfaces of the back surface are coated with an insulating and sound-absorbing material.

* * * * *

UNITED STATES PATENT AND TRADEMARK OFFICE

CERTIFICATE OF CORRECTION

PATENT NO. : 4,721,106

DATED : January 26, 1988

INVENTOR(S) : Gunther Kurtze, et al.

It is certified that error appears in the above-identified patent and that said Letters Patent is hereby corrected as shown below:

IN THE BRIEF DESCRIPTION OF THE DRAWINGS

In column 2, line 16, please delete "ilustrate" and substitute therefor --illustrate--.

IN DETAILED DESCRIPTION OF THE PREFERRED EMBODIMENTS

In column 4, line 9, please delete "wave impact" and substitute therefor --impact wave--.

In column 4, line 10, please delete "wave impact" and substitute therefor --impact wave--.

In column 4, line 19, please delete "incldues" and substitute therefor --includes--.

Signed and Sealed this

Fourteenth Day of February, 1989

*Attest:*

DONALD J. QUIGG

*Attesting Officer*

*Commissioner of Patents and Trademarks*